United States Patent
Haley

(10) Patent No.: US 8,945,606 B2
(45) Date of Patent: Feb. 3, 2015

(54) ORAL ADHERING DISC WITH DIMPLE ON ADHERING SIDE

(75) Inventor: Jeffrey T. Haley, Mercer Island, WA (US)

(73) Assignee: OralHealth Corp., Bellevue, WA (US)

( * ) Notice: Subject to any disclaimer, the term of this patent is extended or adjusted under 35 U.S.C. 154(b) by 625 days.

(21) Appl. No.: 12/287,647

(22) Filed: Oct. 10, 2008

(65) Prior Publication Data

US 2010/0092543 A1 Apr. 15, 2010

Related U.S. Application Data

(63) Continuation of application No. PCT/US2007/009032, filed on Apr. 13, 2007.

(60) Provisional application No. 60/792,121, filed on Apr. 13, 2006.

(51) Int. Cl.
*A61F 13/00* (2006.01)
*A61K 31/04* (2006.01)
*A61K 31/19* (2006.01)
*A61C 19/06* (2006.01)
*A61K 31/245* (2006.01)

(52) U.S. Cl.
CPC .............. *A61K 31/19* (2013.01); *A61C 19/063* (2013.01); *A61K 31/245* (2013.01)
USPC .......................................... 424/435; 514/741

(58) Field of Classification Search
None
See application file for complete search history.

(56) References Cited

U.S. PATENT DOCUMENTS

| | | | | |
|---|---|---|---|---|
| 3,911,099 A | * | 10/1975 | DeFoney et al. | 424/435 |
| 6,197,331 B1 | * | 3/2001 | Lerner et al. | 424/448 |
| 2003/0003140 A1 | * | 1/2003 | Domb et al. | 424/449 |
| 2003/0023313 A1 | * | 1/2003 | Byers | 623/17.18 |
| 2003/0104038 A1 | * | 6/2003 | Hull et al. | 424/443 |
| 2003/0124178 A1 | * | 7/2003 | Haley | 424/449 |
| 2004/0175668 A1 | * | 9/2004 | Abels et al. | 433/10 |
| 2007/0098648 A1 | * | 5/2007 | Haley | 424/48 |

OTHER PUBLICATIONS

MotherNature.com, Canker Sores, pp. 1-8, wayback machine: Dec. 28, 2003.*
Dentist.net, Treatment of Caker Sores, Mouth Sore, Mouth Ulcers, pp. 1-2, wayback machine: Jan. 7, 2004.*
Braces, Instructions and Problems, pp. 1-5, wayback machine: Feb. 31, 2000.*

* cited by examiner

*Primary Examiner* — Scott Long
*Assistant Examiner* — Lyndsey Beckhardt

(57) ABSTRACT

A dissolving oral adhering disc (troche) with a dimple on at least one side to improve adhesion to hard convex surfaces in the mouth, including teeth, orthodontic braces, and gums (keratinized gingiva). The disc may be designed to prevent or treat a sore in the mouth opposite a tooth or brace and/or to release a medication into the mouth, to treat such as sore or to treat or prevent conditions elsewhere in the mouth or throat or stomach.

12 Claims, 2 Drawing Sheets

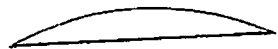
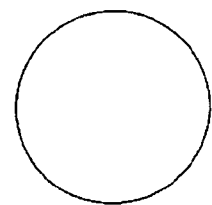
Fig. 1a　　　　　　　　　　Fig. 1b
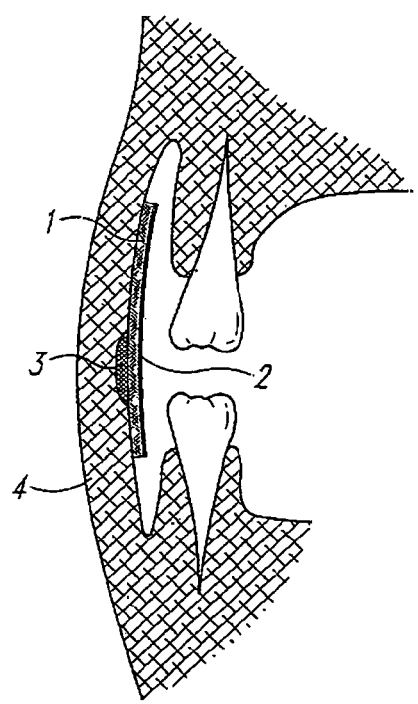
Fig. 2

ORAL ADHERING DISC WITH DIMPLE ON ADHERING SIDE

This application claims priority as a continuation application of international application number PCT/US2007/009032 filed Apr. 13, 2007, which claims priority from U.S. provisional application No. 60/792,121, filed Apr. 13, 2006.

BACKGROUND

To deliver a medication in the mouth over time for treatment of health problems in the mouth or throat, oral patches have been developed.

As used herein, the word "patch" does not include preparations that move about the mouth rather than adhering in one place, such as cough drops or throat lozenges, and therefore do not maintain a high concentration of released medication in the desired spot. Nor does it include preparations that do not hold together as a single item when held in the mouth such as preparations of powder, liquid, paste, viscous liquid gel, or a tablet or troche that crumbles into a powder or paste when chewed or placed in saliva. Conversely, it does include an adherent preparation formed of a hydrocolloid that holds together as a single item when held in the mouth, such as the adherent, soluble oral patch disclosed by the same inventor in U.S. patent application Ser. No. 10/287,843 filed 5 Nov. 2002.

The most significant differences between an oral patch as used herein and other forms of medicinal preparations is that an oral patch is designed to release medication into the mouth over a relatively long period of time, such as 30 minutes or more, and be adherent to stay in one place so that the medication can reach high concentrations along side the patch, and remain in the mouth as a single item that will not spread to be in a plurality of locations in the mouth at one time.

Licorice extract which includes glycyrrhizic acid relieves pain from canker sores without numbing surrounding tissues and promotes healing, although strong enough concentrations to be as effective as desired have an unacceptably strong flavor. An enzyme in saliva, glucuronidase, breaks the glycyrrhizic acid molecule from licorice extract into glucuronic acid plus glycyrrhetinic acid (GTA) and the later acts as an anti-inflammatory.

SUMMARY OF THE INVENTION

Through trials, the inventor has discovered that, directly placing glycyrrhetinic acid ("GTA") which may be extracted from licorice root (glycyrrhiza) in an adhesive oral patch for treatment of ordinary mouth ulcers (also called denture sores, canker sores and aphthous ulcers) is effective for relieving pain and speeding of healing. When GTA is held on a canker sore with an oral patch for longer than 15 minutes, the canker sore pain is significantly reduced and there is no numbing of surrounding tissues. The pain relief continues while eating long enough to complete a meal with reduced pain. The patch with GTA also speeds healing.

GTA base may be used in the oral patch. However, for higher levels of absorption into local tissues and therefore greater effectiveness for the level of drug used (to minimize risks of side effects) it is preferable to use a salt of glycyrrhetinic licorice extract that is water soluble at human mouth temperatures (Soluble Glycyrrhetinic Extract, "SGE"). SGE comprises a group of chemical salts of glycyrrhetinic acid that are soluble in water at human mouth temperatures, including potassium salt of glycyrrhetinic acid and other alkali metal salts of glycyrrhetinic acid.

In one aspect, the invention is a method for treating canker sores by providing patches which, when exposed to saliva in a human mouth, release GTA over more than 30 minutes, and instructing people to hold the patches in their mouths on or near the canker sore for at least 2 or more hours per day. The patch may include a binder ingredient to hold and release the medication.

The binder ingredients may be a combination of gums that dissolve in saliva, such as gum Arabic (acacia gum), carrageenan, xanthan gum, konjac gum, agar, or locust bean gum and non-dissolving food fibers. If the binders are xanthan gum, konjac gum, and cellulose fiber, effective dry weight formulations have between 1% and 10% SGE, such as potassium salt of GTA, between 20% and 55% food grade gelatin, and between 20% and 75% other binders. Another effective formula has 24% SGE with about 5-7% benzocaine and 50-93% gelatin, with acacia gum added on a side intended to be more adherent.

BRIEF DESCRIPTION OF THE DRAWINGS

FIG. 1a shows a side view of an oral patch that completely dissolves (erodes).

FIG. 1b shows a top view of the same oral patch.

FIG. 2 shows a layered oral patch covering a canker sore.

DETAILED DESCRIPTION

Figure 3:
FIG. 3 shows a domed oral patch with a dimple made by pressing powders.

FIG. 1 shows an adhesive oral patch that completely dissolves (more precisely, erodes as the molecules become hydrated). In the mouth, it has a feel and texture like hard gummy candies. It is made with slowly dissolving hydrocolloids so that that it typically lasts in the mouth for at least one to six hours. The patch can be formed in the shape of a tablet or a lozenge or a wafer or any other desired shape. A preferred shape is a thin lentil which may be nearly flat on one side as shown in FIG. 1a.

Another preferred shape for adhering to a tooth or braces that caused a cut that has become or is likely to become an ulcer is a dimpled dome—that is, convex on one side and concave on the other side. An example is shown in cross-section in FIG. 3. The dimple may be a slight concavity. Nine millimeters diameter is a preferred size for such a dimpled dome made by pressing powders, with 0.5 to 1.5 millimeters for the depth of the dimple. For adhering to a bracket of orthodontic braces, such a dimple will allow greater contact with the bracket and wires for better adhesion. For adhering to a tooth, the concave dimple will allow the patch to adhere to a convex tooth surface at the periphery of the patch with multiple points of contact rather than with essentially a single point of contact near the center of a flat or convex patch surface.

A detailed description of a deposited patch and how to make it are disclosed by the same inventor in U.S. patent application Ser. No. 10/287,843 filed 5 Nov. 5, 2002 and published by the US Patent Office. A detailed description of a pressed powders patch made with mucoadhesive hydrocolloids pressed in two layers, one quite adhesive, entitled "Xylitol troches and methods of use" is disclosed by the same inventor in U.S. patent application Ser. No. 60/879,846 filed 11 Jan. 2007 (agent reference 0795-037-02(2)).

To cause the patch to dissolve (erode) very slowly in saliva, a binder that dissolves slowly in saliva is incorporated. Binders that have been tested and found to work well include gelatin, carrageenan (preferably kappa), xanthan gum, konjac gum, agar, gum arabic, and pectin. Other gums similar to those listed, such as locust bean gum which has properties similar to konjac gum, and guar gum should also work.

In addition to causing the patch to erode very slowly in the mouth, the binder also moderates any strong flavors by spreading out over a long period of time the release of that flavor. Consequently, sweeteners and other products to mask strong flavors are not required, although some users prefer a small amount of sweetener and some also prefer the addition of other flavors.

A method of manufacturing the patches of FIG. 1 is to use gum drop manufacturing equipment, squirting a hydrated mixture heated above the gel melting temperature through nozzles onto a sheet of plastic or mold, allowing the patches to cool and gel, and drying the patches. The patches are preferably dried until the water activity level is lower than 0.8 so that the patches will not grow mold or other organisms. The patches are packaged with a hermetic seal to prevent absorption of water moisture from air. The resulting patches are at least 5 mm in each of at least two dimensions, preferably 8-18 mm.

The mixture may be deposited as an array of hot, viscous drops onto a sheet of high temperature plastic or coated paper. The drops are allowed to cool and then the sheets of plastic or coated paper with the drops on them are dried in a drying room. The product is sold still adhered to the plastic or paper and the user pulls it off the plastic or paper.

FIG. 2 shows a bi-layer oral patch comprising a permeable layer 1 and a non-permeable smooth outer layer 2. The oral patch is covering a canker sore 3 in a human cheek 4. The outer layer 2 is preferably smooth to minimize dislodging of the patch. Medication is held in the permeable layer 1 either by using a high viscosity liquid medication that slowly oozes out of the layer or by binding the medication to the layer with slowly dissolving binders such as any of the gums described above, including gelatin. A preferred size for the patch is 18 millimeters, and one or both layers of the patch may include a red pigment to color it like the inside of the mouth.

Alternatively, any of the other oral patches known in the art may be used, such as patches made by heat a thermo gel mixture, extruding a flat sheet, and die cutting.

For higher levels of absorption into local tissues and therefore greater effectiveness for the level of drug used (to minimize risks of side effects) it is preferable to use a water soluble salt of glycyrrhetinic licorice extract (Soluble Glycyrrhetinic Extract, "SGE"). This avoids a drop in pH that would be caused by using pure glycyrrhetinic acid. SGE comprises a group of chemical salts of glycyrrhetinic acid that are soluble in water at human mouth temperatures, including potassium salt of glycyrrhetinic acid and other alkali metal salts of glycyrrhetinic acid.

A preferred quantity of SGE in each patch that lasts 20 minutes to 6 hours is 1% to 10% of the non-water ingredients, most preferably 2-6%. For patches of 0.1 to 0.2 grams dry weight, this is 2-12 mg of SGE, such as potassium salt of glycyrrhetinic acid. For an oral patch made by a tablet pressing process, the preferred size is about 100 to 150 milligrams for total tablet weight and the preferred quantity of SGE is 2.5-4 milligrams.

Glycyrrhetinic acid (GTA) is a mer component of glycyrrhizic acid, which is the negative part of the salt glycyrrhizin, which is a major ingredient in simple water extract of licorice root. When dissolved in water, the glycyrrhizic acid becomes bio-available from the glycyrrhizin. Aided by the enzyme glucuronidase which is in all body fluids including saliva, this component hydrolyzes to release the glycyrrhetinic acid which causes undesirable side effects when taken in too large a quantity. However, in moderate quantities, the anti-inflammatory effect of glycyrrhetinic acid is desirable for reducing pain and speeding healing of ulcers because the quantities required are far below the side effect threshold, especially when a water soluble form of GTA (SGE) is used so that the GTA leaches well out of the patch and passes easily into the epithelium.

The preferred patch formulation is made by combining the GTA extract with collagen and with binder ingredients. Collagen, which is the organic molecule that makes up skin and the lining of the mouth (a form of skin), tends to adhere very well to itself, making it glutinous, and therefore adheres very well to the lining of the mouth. An effective and cost effective form of collagen is food grade gelatin which is made from animal skins. As the collagen molecules slough off the patch while it slowly dissolves (erodes), they tend to adhere to the nearby mouth lining, forming a film. This film significantly reduces the sensitivity of the ulcer, both to touch and to chemical irritants.

Testing shows that, if the binders are xanthan gum, konjac gum, and cellulose fiber, effective dry weight formulations have between 1% and 10% GTA, between 20% and 99% food grade gelatin, between 0% and 75% other binders.

Presented below are conclusions from testing on 49 subjects of the adherent, soluble oral patches with about 7-9% GTA:

Pain relief: Using a patch for 10-15 minutes before a meal reduces pain of the canker sore, and, if used up to commencement of a meal, the pain relief lasts through a typical meal. There is no numbing effect on surrounding tissues.

Catching it early: If the user catches the canker sore early, shorter treatment is required. The sore will often start in a small cut. Some users report that if they apply one patch to a cut for 1-4 hours before there is any sensation of a canker sore, then they will not get a canker sore from the cut. Other times, the sore starts with a feeling that the mucous layer is becoming too thin in a spot before it becomes painful. Some users report that if they apply one patch to that spot, no canker sore develops. Users report that if they begin applying the patch when the canker sore is very small and barely painful, the patches control the pain to the extent that there is no significant pain and healing is accelerated.

Treatment of the tongue: For treatment of the tongue, most users stick a patch (which releases extract on both sides) to the closest tooth. This works particularly well at night.

Braces: Users with braces apply the patch to the braces opposite the canker sore so that the patch is touching the canker sore most of the time and is stuck to the teeth and braces. As it softens, the patch settles into the braces. It will completely dissolve out of the braces in 3-9 hours. All this time it supplies GTA to the sore.

While particular embodiments of the invention have been described above the scope of the invention should not be limited by the above descriptions but rather limited only by the following claims.

What is claimed:

1. A method for making a dimpled, adhering troche that releases an ingredient in a human mouth, comprising:
   pressing powders comprising an adhesive powder and a powder comprising the ingredient to form an oral adhering troche having a convex surface of between 5 and 18 millimeters in at least two dimensions and a concave adhesive surface having a depth of at least 0.5 millimeters, wherein the concave surface is opposite the convex surface; and wherein the concave adhesive surface is for placing against and adhering to a hard surface in a human mouth;
   thereby releasing the ingredient as the troche erodes.

2. The method of claim 1 wherein the hard surface is a tooth.

3. The method of claim 1 wherein the hard surface is an orthodontic brace mounted on a tooth.

4. The method of claim 1 wherein the ingredient comprises a medication.

5. The method of claim 1 wherein the ingredient treats a mouth sore.

6. The method of claim 5 wherein the ingredient comprises benzocaine.

7. The method of claim 1 wherein the adhesive powder comprises gelatin between 50% and 93%.

8. The method of claim 1, wherein the powders are pressed into layers.

9. The method of claim 8, wherein the troche comprises two layers.

10. The method of claim 9, wherein one of the layers comprises an adhesive powder.

11. The method of claim 1, wherein the troche further comprises a binder.

12. The method of claim 11, wherein the binder is acacia gum.

\* \* \* \* \*

UNITED STATES PATENT AND TRADEMARK OFFICE
CERTIFICATE OF CORRECTION

PATENT NO. : 8,945,606 B2  
APPLICATION NO. : 12/287647  
DATED : February 3, 2015  
INVENTOR(S) : Jeffrey T. Haley Page 1 of 1

It is certified that error appears in the above-identified patent and that said Letters Patent is hereby corrected as shown below:

On the Title page, the Assignee should be corrected from "Oralhealth Corp." to "OraHealth Corp."

Signed and Sealed this
Second Day of June, 2015

Michelle K. Lee
*Director of the United States Patent and Trademark Office*